United States Patent [19]
Fukuda et al.

[11] Patent Number: 6,013,184
[45] Date of Patent: *Jan. 11, 2000

[54] DEVICE FOR DEPLETION OF LEUKOCYTES

[75] Inventors: Tatsuya Fukuda; Syuji Terashima, both of Oita, Japan

[73] Assignee: Asahi Medical Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/716,617

[22] Filed: Sep. 19, 1996

[30] Foreign Application Priority Data

Sep. 19, 1995 [JP] Japan ................................. 7-263644

[51] Int. Cl.⁷ .................................................. B01D 24/00
[52] U.S. Cl. ...................... 210/645; 210/257.1; 436/180; 422/100
[58] Field of Search ................... 210/767, 505, 210/257.1; 7/435, 446, 503; 422/44, 48, 100; 436/180

[56] References Cited

U.S. PATENT DOCUMENTS

| | | | |
|---|---|---|---|
| 3,868,973 | 3/1975 | Bierman et al. | 138/43 |
| 3,878,869 | 4/1975 | Yamanouchi et al. | 138/40 |
| 4,105,029 | 8/1978 | Virag | 604/81 |
| 4,620,564 | 11/1986 | Ekholmer | 137/595 |
| 4,810,378 | 3/1989 | Carmen et al. | 210/206 |
| 4,858,127 | 8/1989 | Kron et al. | 73/54.09 |
| 5,265,822 | 11/1993 | Schober, Jr. et al. | 242/388.2 |
| 5,399,268 | 3/1995 | Pall et al. | 210/767 |
| 5,476,587 | 12/1995 | Kuroki et al. | 210/496 |
| 5,630,946 | 5/1997 | Hart et al. | 210/805 |

FOREIGN PATENT DOCUMENTS

| | | |
|---|---|---|
| 0209863 | 1/1987 | European Pat. Off. . |
| 0370584 | 5/1990 | European Pat. Off. . |
| 0408462 | 1/1991 | European Pat. Off. . |
| 0718006A1 | 6/1996 | European Pat. Off. . |
| 3236310A1 | 4/1983 | Germany . |
| 1117348 | 8/1989 | Japan . |
| 1348383 | 3/1974 | United Kingdom . |
| 1403810 | 8/1975 | United Kingdom . |
| 1406388 | 9/1975 | United Kingdom . |
| 2000685 | 1/1979 | United Kingdom . |
| 2061125 | 5/1981 | United Kingdom . |
| 2083757 | 3/1982 | United Kingdom . |
| 2212886 | 8/1989 | United Kingdom . |
| 2254169 | 9/1992 | United Kingdom . |

OTHER PUBLICATIONS

Kelly et al. ("Alterations in viscosity and filterability of whole blood and blood cell subpopulations in diabetic cats", Exp. Eye Res. (1993), 5693), 341–7), month unknown 1993.

Primary Examiner—Jill Warden
Assistant Examiner—Alex Noguerola
Attorney, Agent, or Firm—Birch, Stewart, Kolasch & Birch, LLP

[57] ABSTRACT

A device for preparing leukocyte-depleted products from leukocyte-containing fluid, comprising at least an inlet port, a leukocyte removal filter, an outlet port and a conduit which connects the inlet port, the leukocyte removal filter and the outlet port to the device in this order, wherein a narrow portion for controlling flow rate is provided in the conduit at the downstream side of the leukocyte removal filter.

12 Claims, 3 Drawing Sheets

EFFECTIVE CROSS SECTION

EFFECTIVE CROSS SECTION

EFFECTIVE CROSS SECTION

EFFECTIVE CROSS SECTION

EFFECTIVE CROSS SECTION

EFFECTIVE CROSS SECTION

DEVICE FOR DEPLETION OF LEUKOCYTES

BACKGROUND OF THE INVENTION

1. Field of the Invention

The present invention relates to a device for depletion of leukocytes or white blood cells from leukocyte-containing fluids, especially blood products having a low viscosity, such as whole blood or platelet derivatives, in which a leukocyte removal filter can maintain leukocyte depletion at a high level. The present invention further relates to a method for preparing leukocyte-depleted products using the device.

2. Description of the Related Art

Recent studies on immunology and blood transfusion reveal that adverse post-transfusion reactions are provoked by leukocytes present in blood products. In order to prevent, among others, relatively moderate headache, vomiting, chill, nonhemolytic febrile transfusion reactions, etc., it is recognized necessary to reduce the white cell count infused into a recipient by single transfusion to approximately $10^8$ or less. To satisfy the desired white cell count, leukocytes should be removed until the residual leukocytes decrease to the level of less than $10^{-1}$ to $10^{-2}$.

With regard to graft-versus-host-reactions (GVHR), cytomegalovirus infections and alloimmunization which are severe side effects, it is expected that these adverse effects could be prevented by removing leukocytes until the residual leukocytes become less than $10^{-4}$ to $10^{-6}$.

For these reasons, it is therefore general in blood products to remove leukocytes using a leukocyte removal filter comprising non-woven cloth or porous materials.

A leukocyte removal filter is often employed by mounting the filter to a device for leukocyte depletion, which is equipped with a conduit for connecting the filter and flowing blood therethrough. In general, such a device has an inlet port and an outlet port at the upstream and downstream sides of the leukocyte removal filter, respectively, which ports are connected to the conduit. Such a device for leukocyte depletion equipped with a leukocyte removal filter is employed for direct transfusion to a patient, i.e., putting the device at a patient's bedside, or employed for preparing leukocyte-depleted products at blood centers.

For minimizing a load on patients, leukocyte depletion at a bedside is operated usually by controlling a blood flow rate to a level of approximately 5 to 10 ml/min. On the other hand, a method for leukocyte depletion performed at blood centers or elsewhere to prepare leukocyte-depleted products comprises connecting a device for leukocyte depletion having a leukocyte removal filter mounted thereto to a blood collection bag, in which blood to be treated is put, passing the blood through the filter to remove leukocytes, and recovering leukocyte-depleted products in a transfer bag (bag—bag filtration). Therefore, a distance (head) from the blood collection bag to the transfer bag is generally adjusted to 0.5 to 1.5 meter so that leukocytes are removed by gravity drop.

Where blood products are those having a low viscosity like platelet concentrates, such bag—bag filtration frequently results in an average blood flow rate exceeding 70 ml/min in a conventional device for leukocyte depletion so that leukocytes adhere to a filtering material only with difficulty to reduce its efficiency of leukocyte depletion. It was thus difficult to stably maintain the residual rate of leukocytes to $10^{-4}$ or less.

On the other hand, when too slow an average blood flow rate encounters problems that it takes too much time to prepare leukocyte-depleted products and it is difficult to process a large volume of blood products. Too slow a flow rate in biological products such as blood products means that a contact time of a filtering material with blood cells is prolonged, resulting in the formation of microaggregates due to activation of blood cells and thus leading to reduction in quality of the resulting leukocyte-depleted products. Furthermore, in the case that platelets are recovered as effective components, there is a problem that highly viscous platelets might be adhered to a filtering material to lower the recovery rate of platelets. An additional concern arises that many leukocytes might be adhered to the upper layer of a leukocyte removal filter to cause clotting of the filter with leukocytes so that pores of the filtering material are occluded and the filtering material at the lower layer of the occluded portion might loose the ability of effectively removing leukocytes. Such clotting caused by leukocytes might greatly decrease a blood flow rate or even prevent blood from flowing down.

JP-U-1-117348 discloses a transfusion set having a narrow portion for controlling flow rate which is employed for transfusion of a drug substantially free of solid, such as glucose solution or Ringer's solution. However, this transfusion set is not designed for treating a leukocyte-containing suspension comprising blood cells and viscous plasma components. JP-U-1-117348 does not even suggest any application to a flow rate controlling mechanism for removing leukocytes.

Some devices for leukocyte depletion used at a bedside may have a roller clamp above or beneath a leukocyte removal filter. The roller clamp provided for suitably controlling a transfusion rate applied to patients is a means for gradually adjusting a desired flow rate, while measuring the drop count and blood weight. Accordingly, where a large volume of leukocyte-depleted products are prepared, there arise problems that it takes long and the position of a roller at the roller clamp may change due to a passage resistance of blood during the filtration of blood and hence, a flow rate is liable to change.

In a device for depletion of leukocytes it is also known to control a blood flow rate by decreasing a head. However, according to this method for decreasing a head, the distance between an inlet port and a leukocyte removal filter becomes inevitably short so that difficulties occur in preventing the air from permeating into the filter and in mounting a chamber for removing gels in the device for leukocyte depletion. Furthermore, where the head is too small, filtration must be conducted in some occasion by putting the leukocyte removal filter on the floor or giving a tilt to the filter. In this case, problems encounter that the ability of leukocyte depletion might be reduced due to blood flowing only on one side or a bag might be exchanged only with difficulty.

SUMMARY OF THE INVENTION

The present inventors made extensive investigations to develop a device for depletion of leukocytes which is excellent in handling, and a method for preparing leukocyte-depleted products using the device for depletion of leukocytes. As a result, it has been found that by providing a narrow portion for controlling flow rate at the downstream side of the leukocyte removal filter in the device for depletion of leukocytes, the flow rate can be controlled stably in a simple manner.

In order to stably maintain the residual leukocyte rate at the level of 10–4 or less and operate the leukocyte depletion as quickly as possible in preparing the leukocyte-depleted product using the device for depletion of leukocytes, it has also been found that a fluctuation of the flow rate should be minimized and an average flow rate should be stably kept in the range of 20 to 50 ml/min. Particularly when leukocytes are removed from a leukocyte-containing fluid having a low viscosity, it has been found that the device for depletion of leukocytes having a minimized fluctuation of flow rate and capable of controlling the average flow rate to a desired level in a simple manner can be obtained by locating at the downstream side of the leukocyte removal filter a conduit with a narrow portion for controlling a flow rate, which has a specific range of an effective cross section and a specific range of a ratio of a length to the effective cross section. The present invention has thus been accomplished.

The present invention provides a device for preparing leukocyte-depleted products from leukocyte-containing fluid, comprising at least an inlet port, a leukocyte removal filter, an outlet port and a conduit which connects the inlet port, the leukocyte removal filter and the outlet port to the device in this order, wherein a narrow portion for controlling flow rate is provided in the conduit at the downstream side of the leukocyte removal filter.

The present invention also provides a device for preparing leukocyte-depleted products from leukocyte-containing fluid, comprising at least an inlet port, a leukocyte removal filter, an outlet port and a conduit which connects the inlet port, the leukocyte removal filter and the outlet port to the device in this order, said leukocyte removal filter having a permeability resistance of 20 to 4,900 Pa (2 to 500 mm $H_2O$) and a distance from the inlet port to the outlet port of approximately 0.5 to 3.0 meters, wherein 1) a narrow portion for controlling flow rate is provided in the conduit at the downstream side of the leukocyte removal filter, and
2) said narrow portion for controlling flow rate has an effective cross section in the range of 0.1 to 5.0 mm$^2$ and a ratio of length to the effective cross section in the range of 3 to 400 mm/mm$^2$.

The present invention further provides a method for preparing leukocyte-depleted products which comprises:
using a device for preparing leukocyte-depleted products from leukocyte-containing fluid, comprising at least an inlet port, a leukocyte removal filter, an outlet port and a conduit which connects the inlet port, the leukocyte removal filter and the outlet port to the device in this order, wherein a narrow portion for controlling flow rate is provided in the conduit at the downstream side of the leukocyte removal filter;
supplying the leukocyte-containing fluid from the inlet port; and,
recovering the fluid from the outlet port passed through the leukocyte removal filter.

The present invention also provides a method for preparing leukocyte-depleted products which comprises:
using a device for preparing leukocyte-depleted products from leukocyte-containing fluid, comprising at least an inlet port, a leukocyte removal filter, an outlet port and a conduit which connects the inlet port, the leukocyte removal filter and the outlet port to the device in this order, said leukocyte removal filter having a permeability resistance of 20 to 4,900 Pa (2 to 500 mm $H_2O$), wherein 1) a narrow portion for controlling flow rate is provided in the conduit at the downstream side of the filter, and
2) said narrow portion for controlling flow rate has an effective cross section in the range of 0.1 to 5.0 mm$^2$ and a ratio of length to effective cross section in the range of 3 to 400 mm/mm$^2$;

setting a distance from the inlet port to the outlet port to approximately 0.5 to 2.0 meters,
supplying leukocyte-containing fluid having a viscosity of not greater than 5.5 mPa.s from the inlet port; and,
recovering the fluid from the outlet port passed through the leukocyte removal filter.

PREFERRED EMBODIMENTS OF THE INVENTION

Figure 1:
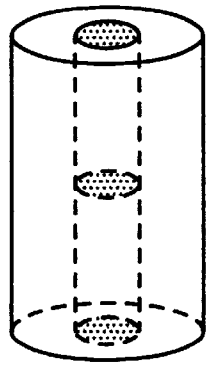
FIG. 1 illustratively shows an embodiment of the narrow portion for controlling flow rate comprising a cylindrical hollow tube.

The conduit as used in the present invention refers to a hollow tube for connecting the inlet port, the leukocyte removal filter, the outlet port and the like, and passing the leukocyte-containing fluid therethrough. Any material may be employed to form the conduit without any limitation, so long as it is a hollow tube functioning to pass the leukocyte-containing fluid and it does not damage blood cells. Among such materials, preferred are organic materials such as polyvinyl chloride, silicone, polyurethane, polyethylene, polysulfone, polyamide, polyester, polystyrene, polypropylene, cellulose acetate, natural rubber and the like, because of excellent processability. The effective cross section of the conduit mounted to the device for depletion of leukocytes is generally in the range of approximately 5.7 to 8.0 mm$^2$.

The narrow portion for controlling flow rate as used in the present invention refers to a portion having a smaller effective cross section than that of the conduit generally used and having a specific ratio of the length to the effective cross section which imparts a substantial flow resistance to the portion so as to filter the leukocyte-containing fluid at a desired flow rate.

The effective cross section at the narrow portion for controlling flow rate refers to the cross section of a portion through which the leukocyte-containing fluid can pass when the narrow portion for controlling flow rate is cut vertically to the direction toward which the leukocyte-containing fluid flows down. Where the narrow portion for controlling flow rate is, for example, cylindrical, the effective cross section means the cross section in which the inner diameter of the cylinder becomes the diameter. The effective cross section can be determined by various methods, e.g., a method which comprises cutting the narrow portion for controlling flow rate vertically to the direction toward which the leukocyte-containing fluid flows down and determining the cross section of the cut section by utilizing an image processor or by taking its pictures. Where the narrow portion for controlling flow rate is, for example, cylindrical, there may be applicable a simple method for determining the effective cross section in which the diameter of the cylinder is measured with a scale or slide calipers.

The length of the narrow portion for controlling flow rate can be determined in the same manner as in determining the effective cross section. Where the effective cross section of the narrow portion for controlling flow rate is definite, the length refers to the length of the portion along which the effective cross section is definite. Where the cross section of the narrow portion for controlling flow rate is gradually decreased or increased to the direction toward which the leukocyte-containing fluid flows down, or where there are protrusions in the narrow portion, the length is used to mean the length of the portion along which the effective cross section is in a definite range.

The value obtained by dividing the length of the narrow portion for controlling flow rate by the effective cross section corresponds to the ratio of the length to the effective cross section as used in the present invention.

When leukocytes are removed from a low viscosity leukocyte-containing fluid, the effective cross section of the narrow portion for controlling flow rate in the present invention is in the range of 0.1 to 5.0 $mm^2$. Where the effective cross section of the narrow portion for controlling flow rate is smaller than 0.1 $mm^2$, an average flow rate of the leukocyte-containing fluid is undesirably likely to be 20 ml/min or less and hence, it takes too much for filtration and adhesion of leukocytes might occur to greatly deviate the flow rate. When the effective cross section exceeds 5.0 $mm^2$, the average flow rate of the leukocyte-containing fluid exceeds 50 ml/min so that the leukocyte removal rate might be undesirably reduced. The effective cross section is therefore preferably in the range of 0.2 to 3.5 $mm^2$, more preferably from 0.5 to 1.8 $mm^2$.

The ratio of length to effective cross section is generally in the range of 3 to 400 $mm/mm^2$. With the ratio of length to effective cross section being less than 3 $mm/mm^2$, an average flow rate would exceed 50 ml/min. When the ratio of length to effective cross section is higher than 400 $mm/mm^2$, an average flow rate would become less than 20 ml/min. Therefore, the ratio of length to effective cross section is preferably in the range of 10 to 400 $mm/mm^2$, more preferably 20 to 300 $mm^2$, and most preferably 80 to 250 $mm/mm^2$.

In particular, where the viscosity of the leukocyte-containing fluid is approximately 2.0 to 5.5 mPa.s, the narrow portion for controlling flow rate has preferably the effective cross section in the range of 0.8 to 5.0 $mm^2$ and the ratio of length to effective cross section in the range of 3 to 100 $mm/mm^2$. In this case, it is preferred that the narrow portion for controlling flow rate be formed with a cylindrical hollow tube having a length of 10 to 200 mm. Further where the leukocyte-containing fluid has a viscosity of less than 2.0 mPa.s, especially about 1.0 to about 2.0 mpa.s, the effective cross section of the narrow portion for controlling flow rate is preferably in the range of 0.1 to 3.5 $mm^2$. In this case, it is preferred that the narrow portion for controlling flow rate be formed with a cylindrical hollow tube having a length of 50 to 200 mm.

Figure 2:
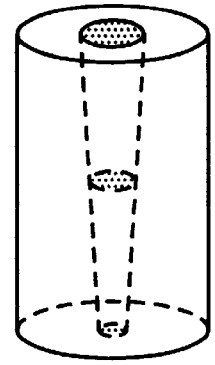
FIG. 2 illustratively shows an embodiment of the narrow portion for controlling flow rate comprising a tapered hollow tube, in which the effective cross section gradually decreases.
Figure 3:
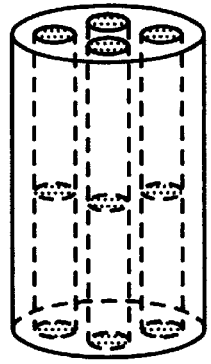
FIG. 3 illustratively shows an embodiment of the narrow portion for controlling flow rate comprising a cylindrical hollow tube having a plurality of small effective cross sections.
Figure 4:
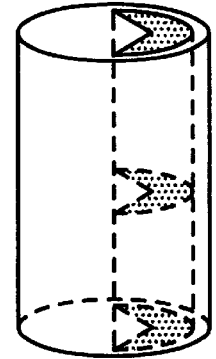
FIG. 4 illustratively shows an embodiment of the narrow portion for controlling flow rate comprising a hollow tube, in which only one side of the conduit forms the narrow portion.
Figure 5:
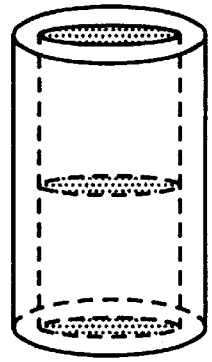
FIG. 5 illustratively shows an embodiment of the narrow portion for controlling flow rate comprising an elliptic hollow tube.

FIGS. 1 through 5 illustratively show representative embodiments of the narrow portion for controlling flow rate in the present invention. FIG. 1 shows the narrow portion for controlling flow rate formed with a cylindrical hollow tube. FIG. 2 shows the narrow portion for controlling flow rate comprising a tapered hollow tube, in which the effective cross section gradually decreases. FIG. 3 shows the narrow portion for controlling flow rate comprising a cylindrical hollow tube having a plurality of small effective cross sections. FIG. 4 shows the narrow portion for controlling flow rate comprising a hollow tube, in which only one side of the conduit forms the narrow portion. FIG. 5 shows the narrow portion for controlling flow rate comprising an elliptic hollow tube.

The narrow portion for controlling flow rate in the present invention may be formed by inserting into the conduit a hollow tube having the effective cross section as given above in the given range of the ratio of the length to the effective cross section. Alternatively, the conduit molded into such a hollow tube may also be employed. Furthermore, the conduit may be compressed and deformed by an external force using an appropriate equipment to have the effective cross section as defined above in the given range of the ratio of the length to the effective cross section.

Where the narrow portion for controlling flow rate comprising a hollow tube is inserted into the conduit, the hollow tube may be prepared with a material that is the same as or different from the conduit. The insertion may be made, for example, by independently molding the hollow tube and the conduit and then connecting the hollow tube to the conduit using an appropriate connecting equipment.

Figure 7:
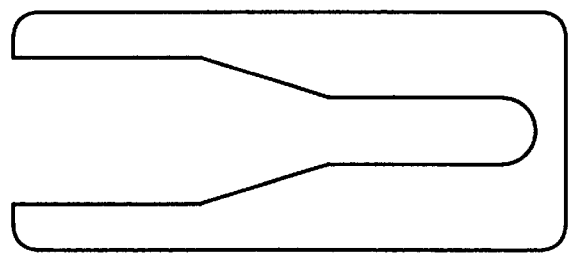
Figure 8:
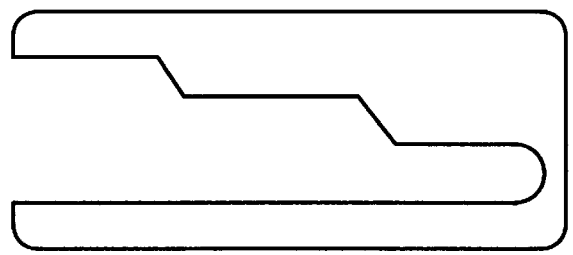
Figure 9:
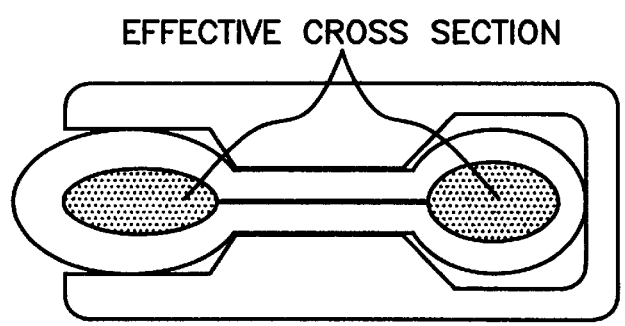
FIG. 9 illustratively shows an embodiment of the conduit deformed under compression by the slide clamp.

More specifically, a cylindrical hollow tube having a uniform cross section, an inner diameter of approximately 0.4 to 2.5 mm, preferably 0.5 to 2.1 mm, more preferably 0.8 to 1.5 mm and a length of approximately 10 to 200 mm, preferably 50 to 200 mm, more preferably 50 to 150 mm, is inserted into the conduit. The hollow tube inserted has the ratio of length to effective cross section in the range of 3 to 400 $mm/mm^2$, preferably 10 to 400 $mm/mm^2$.

Where the conduit is compressed and deformed by an external force using an appropriate equipment to have the effective cross section as defined above in the given range of the ratio of length to effective cross section, a slide clamp, for example, is used specifically. The narrow portion for controlling flow rate can be prepared in a simple manner in a short period of time to have the definite ranges of the effective cross section and the ratio of length to effective cross section, merely by inserting the conduit between the slide clamp having a definite thickness. Accordingly, the slide clamps are preferred equipments. The slide clamps are illustratively shown in FIGS. 6 to 8. FIG. 9 illustratively shows the conduit compressed and deformed using the slide clamp shown in FIG. 6.

Typical embodiments of the device for depletion of leukocytes of the present invention include a device comprising the conduit in which the hollow tube having the effective cross section and the ratio of length to effective cross section as defined above has been previously inserted and a device which can form the narrow portion for controlling flow rate as defined above using an appropriate equipment such as a slide clamp. The device for depletion of leukocytes of the present invention does not embrace such a device that forms the narrow portion for controlling flow rate as defined above in the conduit, for example, as a result of gradually controlling to a desired flow rate while measuring the drop count or blood weight during the filtration of the leukocyte-containing fluid.

In order to decrease the effective cross section of the conduit by compressing and deforming the conduit by an external force using an equipment such as a slide clamp, additional operations for compression and deformation are required. Accordingly, where importance is attached to a simple operation, it is preferred to use the device for depletion of leukocytes previously having mounted thereto the conduit having the narrow portion for controlling flow rate which meets the definition above. It is more preferred to use the device for depletion of leukocytes with the conduit having inserted therein the narrow portion for controlling flow rate comprising a hollow tube which meets the above definition. Particularly when the hollow tube is previously inserted into the conduit, it is advantageous to use a cylindrical hollow tube because of easy molding and high precision in molding.

The conduit at the downstream side of the leukocyte removal filter may have the narrow portion for controlling flow rate with an effective cross section of 0.1 to 5.0 mm$^2$ at only one site or at plural sites. Where the narrow portion for controlling flow rate is placed at plural sites, it may be sufficient to meet the criterion of the present invention that the sum of the ratios of length to effective cross section at the sites is in the range of 3 to 400 mm/mm$^2$. However, in order to minimize the labor to prepare the device for depletion of leukocytes, it is preferred to provide the narrow portion for controlling flow rate at only one site.

In the present invention, it is required that the narrow portion for controlling flow rate should be positioned at the downstream side of the leukocyte removal filter to prevent clotting of the narrow portion for controlling flow rate, due to gel-like substances or microaggregates possibly present in the leukocyte-containing fluid. Such gel-like substances or micro-aggregates are removed by the leukocyte removal filter so that clotting at the narrow portion for controlling flow rate can be prevented thereby to minimize a possible fluctuation in a flow rate.

Furthermore, where the conduit has therein a portion having its effective cross section in the range of 0.1 to 5.0 mm$^2$ at the upstream side of the leukocyte removal filter, such a device is included by the device for depletion of leukocytes of the present invention, so long as the ratio of length to effective cross section of the portion is less than 1.0 time the ratio of length to effective cross section of the narrow portion for controlling flow rate. This is because even if the conduit has therein a portion having its effective cross section of 0.1 to 5.0 mm$^2$ at the upstream side of the leukocyte removal filter, the flow rate of the leukocyte-containing fluid is controlled by narrow portion for controlling flow rate as long as its ratio of length to effective cross section is smaller than the ratio of length to effective cross section of the narrow portion for controlling flow rate. It is preferred that the ratio of length to effective cross section of such a portion located at the upstream side of the leukocyte removal filter be not greater than 0.8 time, more preferably not greater than 0.5 time the ratio of length to effective cross section of the narrow portion for controlling flow rate. However, where the effective cross section is 5.0 mm$^2$ or less, a substantial flow resistance occurs in the leukocyte-containing fluid having a low viscosity. It is thus preferred that the effective cross section of the conduit at the upstream side of the leukocyte removal filter be greater than 5.0 mm$^2$. The occurrence of such a substantial flow resistance in the conduit at the upstream side of the leukocyte removal filter results in a slow rate of the leukocyte-containing fluid supplied to the leukocyte removal filter so that the air remains in the leukocyte removal filter. As the result, the fluid flows down at only one side of the leukocyte removal filter. Then there is a concern that the leukocyte depletion efficiency might be reduced.

The inlet port as used in the present invention refers to a means for connecting the device for depletion of leukocytes of the present invention to a bag or bottle packed with the leukocyte-containing fluid and supplying the leukocyte-containing fluid into the device for depletion of leukocytes. As the inlet port, there may be employed a plastic needle, a metal needle and the like conventionally used for blood products. The inlet port may be provided not only at one site but also at a plurality of sites so that a plurality of bags packed with the leukocyte-containing fluid can be conveniently connected to these sites. The outlet port as used in the present invention refers to a means for leading the leukocyte-depleted product to a transfer bag, etc.

The leukocyte removal filter mounted in the device for depletion of leukocytes of the present invention is a filter comprising such a structure or construction that can capture leukocytes in the leukocyte-containing fluid but hardly captures other blood components necessary for transfusion. The filter is preferably filled up with a filtering material such as a fibrous medium, a spongy structure, a particulate medium, etc. Preferred examples of such materials that can construct the filter include Sepacell$^R$ PLS (Asahi Medical Co., Ltd.), LRP™ (Pall Co., Ltd.), Imuguard$^R$ III-PL (Terumo Co., Ltd.) and the like.

Upon filtration of the leukocyte-containing fluid having a low viscosity using the device for depletion of leukocytes equipped with the narrow portion for controlling flow rate as defined above, it is necessary to keep the permeation resistance of the filter in the range of 20 to 4,900 Pa (2 to 500 mmH$_2$O).

The permeation resistance of the leukocyte removal filter herein is used to mean a pressure loss when air passes at a flow rate of 1.5 liter/min through the leukocyte removal filter at an ambient temperature of 20 to 25° C. for 20 to 30 seconds. Where the permeation resistance is less than 20 Pa (2 mmH$_2$O), it means that the pores of the filtering material are large or the amount of the filtering material is insufficient; this is not preferred since there is a concern that the leukocyte depletion efficiency might be poor. Where the permeation resistance exceeds 500 mmH$_2$O, it means that the pores of the filtering material are small or the amount of the filtering material is too much; this is not preferred since there is a concern that clotting or reduction in the flow rate might be caused. A preferred permeation resistance is in the range of 50 to 2,900 Pa (5 to 300 mmH$_2$O), more preferably in the range of 150 to 2,500 Pa (15 to 250 mmH$_2$O).

The device for depletion of leukocytes equipped with the narrow portion for controlling flow rate of the present invention is advantageously employed when leukocytes present in the leukocyte-containing fluid with low viscosity of 5.5 mPa.s or less, preferably approximately 1.0 to 2.0 mPa.s, are removed by bag—bag filtration at a head in the range of 0.5 to 2.0 meters, preferably 0.5 to 1.5 meter, more preferably 0.7 to 1.3 meter.

The viscosity as used in the present invention means a viscosity measured at 35 to 37° C. in a shear rate of 230 s$^{-1}$.

The leukocyte-containing fluid having a viscosity of 5.5 mPa.s or less is used to specifically mean blood products such as whole blood (WB), platelet concentrates (PC), platelet rich plasma (PRP), platelet poor plasma (PPP), fresh frozen plasma (FFP). The device for depletion of leukocytes equipped with the narrow portion for controlling flow rate of the present invention can be advantageously employed for removing leukocytes present in blood products having a viscosity of 2 mPa.s or less, especially PC, PRP, PPP or FFP, through bag—bag filtration.

The average flow rate as used in the present invention refers to the value obtained by dividing the volume of the recovered leukocyte-depleted product by the period of time required for filtration of the leukocyte-containing fluid. That is, a filtering time is the period of time required from the point at which the leukocyte-depleted product began to be discharged into a container for recovery of the leukocyte-depleted product to the point at which the leukocyte-containing fluid runs out of the container in which the leukocyte-containing fluid has been put; the value is obtained by dividing the amount of the leukocyte-depleted product recovered during the filtering time by the filtering time.

The device for depletion of leukocytes of the present invention may also be equipped with a chamber or with a pinch clamp. The chamber equipped at the upstream side of the leukocyte removal filter is effective for preventing the air from permeating into the filter. A chamber with mesh therein can remove gel-like substances through the mesh thereby to reduce a possible clotting of the leukocyte removal filter with such gel-like substances. A pinch clamp can temporarily stop the flow of the leukocyte-containing fluid in the device for depletion of leukocytes and can be used when a bag is being exchanged, etc.

The device for depletion of leukocytes of the present invention and the method for preparing leukocyte-depleted products using the device are used at blood centers or elsewhere mainly for bag—bag filtration. The device and method of the present invention may also be applicable to the closed system where the leukocyte-depleted products can be prepared aseptically.

Using the device for depletion of leukocytes of the present invention, the leukocyte-containing fluid having a viscosity as low as 5.5 mPa.s or less can be filtered by controlling the average flow rate to 20 to 50 ml/min in a simple operation. In addition, fluctuation in the flow rate can be minimized. As the consequence, the residual leukocyte rate can be reduced stably to $10^{-4}$ or less. The device for depletion of leukocytes of the present invention has a sufficient length between the inlet and outlet ports so as to secure a head of 0.5 to 2.0 meters. Therefore, it is easy to handle bag exchange and mount a chamber to the device. It is unnecessary to perform filtration by putting the leukocyte removal filter on the floor or by giving a tilt to the filter. For these reasons, it is so little chance to cause the leukocyte-containing fluid flowing only at one side of leukocyte removal filter. The leukocyte depletion ability of the leukocyte removal filter can thus be sufficiently exhibited.

The device for depletion of leukocytes of the present invention and the method for preparing the leukocyte depleted products of the present invention are described in more detail with reference to the following Examples and Comparative Examples. However, the following Examples are not deemed to be limiting the present invention.

EXAMPLES 1 to 5 AND COMPARATIVE EXAMPLES 1 TO 4

Figure 10:
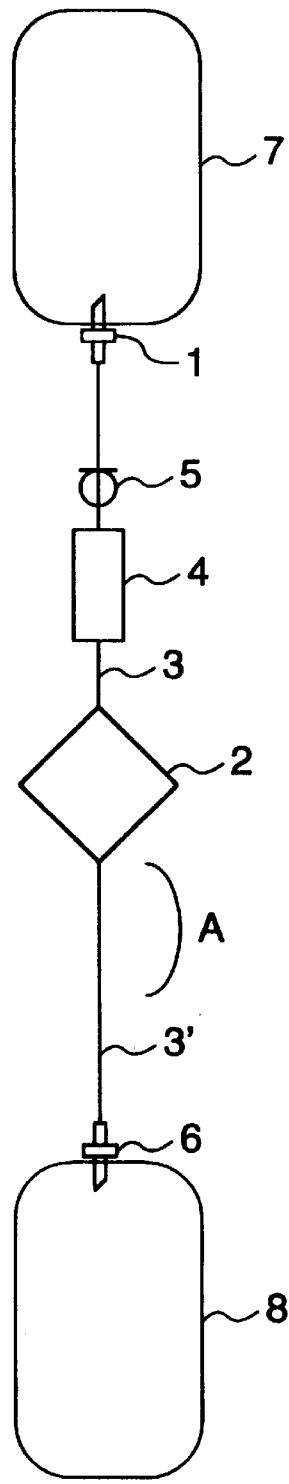
FIGS. 10 and 11 illustratively show the basic construction of the device for depletion of leukocytes according to the present invention, respectively.

Using a device shown in FIG. 10 which had an inlet port (1), a leukocyte removal filter (2), an outlet port (6), conduits (3) and (3'), a chamber with mesh (4) and a pinch clamp (5), a filtrating time, an average flow rate and a residual leukocyte rate were determined. Cylindrical hollow tubes having different inner diameter and different length from each other were each inserted into the conduit (3') at Portion A. For the remaining portions of the conduits there was employed a hollow tube having an inner diameter of 2.9 mm. A blood collection bag (7) which contained CPD solution-added platelet concentrates (blood viscosity of 1.3 mPa.s, blood volume of 400 ml, after storage for 3 days) as the leukocyte-containing fluid was connected to a transfer bag (8) via the device described above and bag—bag filtration was performed at room temperature by gravity drop at a head of 1 meter.

The weight (g) of the leukocyte-depleted product recovered in the transfer bag (8) was divided by 1.030. The thus obtained value was further divided by the filtering time (min.) to determine the average flow rate. Division of the weight of the recovered leukocyte-depleted product by 1.030 was because platelet concentrates have a specific gravity of approximately 1.030.

As a leukocyte removal filter (2), there was employed a filter having a permeation resistance of 245 Pa (25 mmH$_2$O), obtained by packing a container having an inlet port and an outlet port of blood, with non-woven cloth of polyethylene terephthalate. The filter was coated with a copolymer of hydroxyethyl methacrylate (HEMA) and dimethylaminoethyl methacrylate (DM) (mol contents of HEMA and DM are 97 mol % and 3 mol %, respectively) and provided for testing.

The leukocyte concentration in the leukocyte-containing fluid was determined using an optical microscope after staining leukocytes with Turk solution.

The leukocyte concentration in the leukocyte-depleted product was determined using a fluoromicroscope after staining leukocytes with acridine orange solution.

According to the following equation, the residual leukocyte rate was determined based on the leukocyte concentrations in the leukocyte-containing fluid and in the leukocyte-depleted product, the blood volume and the recovered volume.

Residual leukocyte rate={(leukocyte concentration in the leukocyte-depleted product)×(recovered volume)}/{(leukocyte concentration in the leukocyte-containing fluid)×(blood volume)}

The results obtained in Examples 1 to 5 and Comparative Examples 1 to 4 are shown in Table 1.

TABLE 1

| | Conduit inserted into Portion A | | | | | | Residual leuko-cyte rate*[2] (−log) |
|---|---|---|---|---|---|---|---|
| | Inner diameter (mm) | Length (mm) | Cross section*[1] (mm$^2$) | Length/ Cross section (mm/mm$^2$) | Filtering time (min) | Average flow rate (ml/min) | |
| Ex. 1 | 0.8 | 25 | 0.50 | 50 | 8.6 | 43.3 | 4.1 |
| Comp. Ex. 1 | 0.8 | 250 | 0.50 | 500 | 32.7 | 11.4 | 4.5 |
| Comp. Ex. 2 | 0.8 | 1.3 | 0.50 | 2.6 | 4.8 | 78.5 | 3.0 |
| Ex. 2 | 0.8 | 50 | 0.50 | 100 | 9.9 | 37.7 | 4.2 |
| Comp. Ex. 3 | 2.7 | 570 | 5.72 | 100 | 4.7 | 79.6 | 2.8 |
| Comp. Ex. 4 | 0.3 | 7 | 0.07 | 100 | 53.3 | 7.0 | 4.6 |
| Ex. 3 | 0.8 | 100 | 0.50 | 200 | 11.8 | 31.6 | 4.4 |

TABLE 1-continued

| | Conduit inserted into Portion A | | | | | Resid- |
|---|---|---|---|---|---|---|
| | Inner diameter (mm) | Length (mm) | Cross section*[1] (mm$^2$) | Length/ Cross section (mm/ mm$^2$) | Filtering time (min) | Average flow rate (ml/ min) | ual leukocyte rate*[2] (−log) |
| Ex. 4 | 1.0 | 150 | 0.79 | 191 | 11.1 | 33.5 | 4.3 |
| Ex. 5 | 1.5 | 240 | 1.77 | 136 | 10.4 | 35.8 | 4.3 |

*[1] The cross section means the effective cross section at the narrow portion.
*[2] The residual leukocyte rate is expressed by logarithm (−log (residual leukocyte rate)).

COMPARATIVE EXAMPLE 5

A filtering time, average flow rate and residual leukocyte rate were determined using the same device and method as in Example 3, except that the cylindrical hollow tube used as the narrow portion for controlling flow rate in Example 3 was arranged to position at the upstream side of the leukocyte removal filter.

As the result, the filtering time was 31.1 minutes. The flow rate was gradually decreased after filtration began and the average flow rate became 12.0 ml/min. The residual leukocyte rate was $10^{-2.8}$. It is considered that microaggregates present in the leukocyte-containing fluid gradually accumulate at the narrow portion to cause clotting, which resulted in a decreased flow rate. It is also considered that due to the narrow portion located at the upstream side, air remains in the leukocyte removal filter so that the fluid flows only at one side of leukocyte removal filter, whereby the residual leukocyte rate exceeded $10^{-4}$.

EXAMPLE 6

Figure 6:
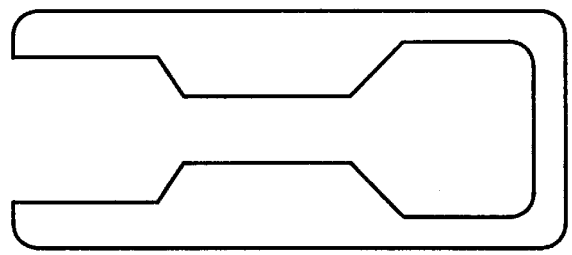
FIGS. 6 to 8 illustratively show embodiments of slide clamp, respectively.
Figure 11:
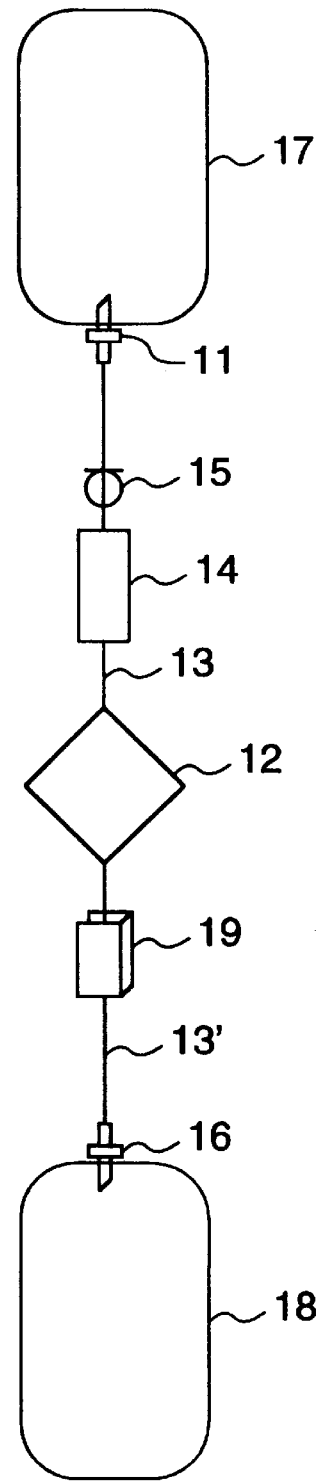

Using a device shown in FIG. 11 which had an inlet port (11), a leukocyte removal filter (12), an outlet port (16), conduits (13) and (13'), a chamber with mesh (14), a pinch clamp (15), a slide clamp (19) shown in FIG. 6, a blood collection bag (17) and a transfer bag (18), a time for filtration, an average flow rate and a residual leukocyte rate were determined. The conduits (13) and (13') were constructed with hollow tubes having an inner diameter of 2.9 mm and, a head was made 1 meter. Bag-bag filtration was conducted using the same device and method as in Examples 1 to 5, except for using a slide clamp (19).

The effective cross section of the portion compressed by the slide clamp was 0.37 mm$^2$ and the ratio of length to effective cross section ratio was 16.2 mm/mm$^2$.

Thus, the filtering time, average flow rate and residual leukocyte rate were 11.1 minutes, 33.5 ml/min and $10^{-4.2}$, respectively.

EXAMPLE 7

After Sepacell$^R$ PLS5N (Asahi Medical Co., Ltd.) was mounted to the device shown in FIG. 10 as the leukocyte removal filter, its filtering time, average flow rate and residual leukocyte rate were determined.

A cylindrical hollow tube having the effective cross section of 0.5 mm$^2$ and the ratio of length to effective cross section ratio of 100 mm/mm$^2$ was inserted into the conduit (3') at Portion A. For the remaining portions of the conduit there was employed a hollow tube having an inner diameter of 2.9 mm. The CPD solution-added platelet concentrates (blood viscosity of 1.3 mPa.s, blood volume of 200 ml, after storage for 2 days) was used as the leukocyte-containing fluid and subjected to bag—bag filtration at room temperature by gravity drop at a head of 1 meter.

Thus, the filtering time, average flow rate and residual leukocyte rate were 6.4 minutes, 27.8 ml/min and $10^{-4.3}$, respectively.

EXAMPLE 8

After LRP6™ (Pall Co., Ltd.) was mounted to the device shown in FIG. 10 as the leukocyte removal filter, its filtering time, average flow rate and residual leukocyte rate were determined.

Bag-bag filtration was conducted using the same device and method as in Example 7, except for using the different leukocyte removal filter.

Thus, the filtering time, average flow rate and residual leukocyte rate were 5.7 minutes, 31.9 ml/min and $10^{-4.1}$, respectively.

EXAMPLE 9 AND COMPARATIVE EXAMPLE 6

Using a device shown in FIG. 10, a filtering time, an average flow rate, a change in flow rate with passage of time and a residual leukocyte rate were determined. Cylindrical hollow tubes having different inner diameter and different length from each other were each inserted into the conduit (3') at Portion A. For the remaining portions of the conduits there was employed a hollow tube having an inner diameter of 2.9 mm. A whole blood with 63 ml of CDP added thereto (blood viscosity of 4.0 mPa.s, blood volume of 513 ml, after storage for 20 hours) was used as the leukocyte-containing fluid. Bag-bag filtration was conducted at room temperature by gravity drop at a head of 1.3 meter.

The weight (g) of the leukocyte-depleted product recovered was divided by 1.052. The thus obtained value was further divided by the filtering time (min) to determine the average flow rate. Furthermore, the amount of the leukocyte-depleted product recovered was measured in 5-minute intervals to examine a change in flow rate with passage of time. Division of the weight of the recovered leukocyte-depleted product by 1.052 was because the whole blood had a specific gravity of approximately 1.052.

As a leukocyte removal filter (2), there was employed a filter having a permeation resistance of 539 Pa (55 mmH$_2$O), obtained by packing a container having an inlet port and an outlet port of blood, with non-woven cloth of polyethylene terephthalate.

The leukocyte concentration in the leukocyte-containing fluid was determined in a manner similar to Examples 1 to 5. The leukocyte concentration in the leukocyte-depleted product was determined by Nageotte method.

The results of Example 9 and Comparative Example 6 are shown in Tables 2 and 3.

As shown in Table 3, the change in flow rate in Comparative Example 6 with passage of time was larger than in Example 9, suggesting that it is highly likely to cause clotting due to leukocytes accumulated at the upper portion of the leukocyte removal filter.

TABLE 2

| | Conduit inserted into Portion A | | | | | Residual leukocyte rate*2 (−log) |
|---|---|---|---|---|---|---|
| | Inner diameter (mm) | Length (mm) | Cross section*1 (mm²) | Length/Cross section (mm/mm²) | Filtering time (min) | Average flow rate (ml/min) | |
| Ex. 9 | 2.0 | 50 | 3.14 | 16 | 16.4 | 28.7 | 4.7 |
| Comp. Ex. 6 | 0.8 | 220 | 0.50 | 440 | 87.0 | 5.4 | 4.9 |

*1 The cross section means the effective cross section at the narrow portion.
*2 The residual leukocyte rate is expressed by logarithm (−log (residual leukocyte rate)).

TABLE 3

| | Change in flow rate with passage of time | | | | | | |
|---|---|---|---|---|---|---|---|
| | 5 mins | 10 mins | 15 mins | 20 mins | 25 mins | 80 mins | 85 mins |
| Ex. 9 | 28.7 | 28.7 | 28.6 | — | — | — | — |
| Comp. Ex. 6 | 10.1 | 9.8 | 9.3 | 8.7 | 8.1 | 1.6 | 0.8 |

EXAMPLES 10 AND 11

The stability of average flow rate was evaluated using a device having inserted the narrow portion for controlling flow-rate as shown in Example 9 at the portion of the conduit (3') as shown in FIG. 10 (in Example 10) and using the same device as in Example 6 having a slide clamp (19) as shown in FIG. 11 (in Example 11). As the leukocyte-containing fluid and the leukocyte removal filter, there were employed those as in Example 9. Bag-bag filtration was performed by gravity drop at a head of 1.3 meter. Filtration was carried out 3 times in each Example. The results are shown in Table 4.

The results shown in Table 4 reveal that in Examples 10 and 11, the average flow rate could be controlled to the range of 20 to 50 ml/min in all of the 3 runs.

TABLE 4

| | Average Flow Rate (ml/min) | | | Average of 3 runs ± standard deviation (ml/min) |
|---|---|---|---|---|
| | Run 1 | Run 2 | Run 3 | |
| Ex. 10 | 29.5 | 28.2 | 27.0 | 28.2 ± 1.02 |
| Ex. 11 | 28.2 | 25.7 | 35.6 | 29.8 ± 4.20 |

What is claimed is:

1. A device for preparing leukocyte-depleted products from leukocyte-containing fluid, comprising at least an inlet port, a leukocyte removal filter, an outlet port, a first conduit which connects the inlet port and the leukocyte removal filter and a second conduit which connects the leukocyte removal filter and the outlet port said leukocyte removal filter having a permeability resistance of 20 to 4,900 Pa (2 to 500 mm $H_2O$) and a distance from the inlet port to the outlet port of approximately 0.5 to 3.0 meters, wherein
   1) a flow opening portion comprising a cylindrical hollow tube for controlling flow rate having an opening cross section narrower than that of the second conduit and having a fixed, over time, length is provided in the second conduit;
   2) said cylindrical hollow tube has a fixed, over time, effective cross section in the range of 0.1 to 5.0 $mm^2$ over its length, a ratio of length to effective cross section in the range of 10 to 400 $mm/mm^2$, and a fixed length of 10 to 200 mm; and
   3) a flow rate can be adjusted to 20–50 ml/min.

2. A device according to claim 1, wherein the effective cross section of the first conduit at the upstream side of the leukocyte removal filter is larger than 5.0 $mm^2$.

3. A device according to claim 1, wherein a portion having its effective cross section in the range of 0.1 to 5.0 $mm^2$ is contained in the first conduit at the upstream side of the leukocyte removal filter and the ratio of length to effective cross section of said portion is less than 1.0 time the ratio of length to effective cross section of the flow opening portion for controlling flow rate.

4. A device according to claim 1, which further comprises a chamber at the upstream side of the leukocyte removal filter.

5. A device according to claim 1, wherein said flow opening portion for controlling flow rate has an effective cross section in the range of 0.1 to 3.5 $mm^2$.

6. A device according to claim 5, wherein said flow opening portion for controlling flow rate comprises a cylindrical hollow tube having a length of 50 to 200 mm.

7. A device according to claim 1, wherein the fixed length of the flow opening portion is in the range of 10 to 200 mm.

8. A method for preparing leukocyte-depleted products which comprises:
   using a device for preparing leukocyte-depleted products from leukocyte-containing fluid, comprising at least an inlet port, a leukocyte removal filter, an outlet port, a first conduit which connects the inlet port and the leukocyte removal filter and a second conduit which connects the leukocyte removal filter and the outlet port, said leukocyte removal filter having a permeability resistance of 20 to 4,900 Pa (2 to 500 mm $H_2O$), wherein
   1) a flow opening portion comprising a cylindrical hollow tube for controlling flow rate having an opening cross section narrower than that of the second conduit and having a fixed length, over time, is provided in the second conduit, and
   2) said cylindrical hollow tube has a fixed, over time, effective cross section in the range 0.1 to 5.0 $mm^2$ over its length, a ratio of length to effective cross section in the range of 10 to 400 $mm/mm^2$ and a fixed length of 10 to 200 mm;
   setting a distance from the inlet port to the outlet port to approximately 0.5 to 2.0 meters,
   supplying leukocyte-containing fluid having a viscosity of not greater than 5.5 mPa.s from the inlet port; and,
   recovering the fluid from the outlet port passed through the leukocyte removal filter in a flow rate of approximately 20 to 50 ml/min.

9. A method according to claim 8, wherein said leukocyte-containing fluid is selected from the group consisting of whole blood, platelet concentrates, platelet rich plasma, platelet poor plasma and fresh frozen plasma.

10. A method according to claim 8, wherein said leukocyte-containing fluid has a viscosity of approximately 1.0 mPa.s to 2.0 mPa.s, both inclusive.

11. A method according to claim 10, wherein said leukocyte-containing fluid is selected from the group consisting of platelet concentrates, platelet rich plasma, platelet poor plasma and fresh frozen plasma.

12. A method according to claim 8, wherein the fixed length of the flow opening portion is in the range of 10 to 200 mm.

* * * * *